United States Patent
Cooper et al.

(10) Patent No.: US 10,821,147 B2
(45) Date of Patent: Nov. 3, 2020

(54) PRINTABLE CANNABINOID AND TERPENE COMPOSITIONS

(71) Applicant: Canopy Growth Corporation, Ontario (CA)

(72) Inventors: Jonathan Michael Cooper, Denver, CO (US); Kurt Aron Levy, Dillon, CO (US)

(73) Assignee: Canopy Growth Corporation, Ontario (CA)

( * ) Notice: Subject to any disclaimer, the term of this patent is extended or adjusted under 35 U.S.C. 154(b) by 0 days.

(21) Appl. No.: 16/060,007

(22) PCT Filed: Dec. 7, 2016

(86) PCT No.: PCT/US2016/065455
§ 371 (c)(1),
(2) Date: Jun. 6, 2018

(87) PCT Pub. No.: WO2017/100369
PCT Pub. Date: Jun. 15, 2017

(65) Prior Publication Data
US 2019/0030101 A1    Jan. 31, 2019

Related U.S. Application Data

(63) Continuation of application No. 15/055,499, filed on Feb. 26, 2016, now abandoned.

(60) Provisional application No. 62/354,463, filed on Jun. 24, 2016, provisional application No. 62/348,114, filed on Jun. 9, 2016, provisional application No. 62/347,558, filed on Jun. 8, 2016, provisional application No. 62/264,281, filed on Dec. 7, 2015.

(51) Int. Cl.

| | | |
|---|---|---|
| A61K 36/185 | (2006.01) |
| A61K 31/122 | (2006.01) |
| A61K 31/353 | (2006.01) |
| A61K 33/00 | (2006.01) |
| A61K 31/01 | (2006.01) |
| A61K 31/015 | (2006.01) |
| A61K 31/045 | (2006.01) |
| A61K 31/05 | (2006.01) |
| A61K 31/35 | (2006.01) |
| A61K 31/352 | (2006.01) |

(52) U.S. Cl.
CPC ............ *A61K 36/185* (2013.01); *A61K 31/01* (2013.01); *A61K 31/015* (2013.01); *A61K 31/045* (2013.01); *A61K 31/05* (2013.01); *A61K 31/122* (2013.01); *A61K 31/35* (2013.01); *A61K 31/352* (2013.01); *A61K 31/353* (2013.01); *A61K 33/00* (2013.01); *A61K 2300/00* (2013.01)

(58) Field of Classification Search
CPC ................................................... A61K 36/185
USPC ........................................................ 514/454
See application file for complete search history.

(56) References Cited

U.S. PATENT DOCUMENTS

| | | |
|---|---|---|
| 4,837,228 A | 6/1989 | Elsohly et al. |
| 5,891,469 A | 4/1999 | Amselem |
| 6,982,282 B2 | 1/2006 | Lambert et al. |
| 7,923,026 B2 | 4/2011 | Moschwitzer |
| 8,790,719 B2 | 7/2014 | Parolaro et al. |
| 2003/0101902 A1* | 6/2003 | Reitnauer ............ A01J 27/005 106/31.31 |
| 2006/0257463 A1* | 11/2006 | Elsohly .................. A61K 9/006 424/449 |
| 2008/0193725 A1 | 8/2008 | Saint-Romain |
| 2009/0098192 A1 | 4/2009 | Fuisz |
| 2009/0133704 A1 | 5/2009 | Strickland et al. |
| 2010/0298579 A1 | 11/2010 | Steup et al. |
| 2011/0052694 A1 | 3/2011 | Stinchcomb et al. |
| 2012/0004251 A1 | 1/2012 | Whalley et al. |
| 2013/0059018 A1 | 3/2013 | Parolaro et al. |
| 2013/0276779 A1* | 10/2013 | Hale ...................... A61K 9/007 128/200.14 |
| 2014/0100269 A1 | 4/2014 | Goskonda et al. |
| 2014/0221469 A1 | 8/2014 | Ross et al. |
| 2014/0243405 A1 | 8/2014 | Whalley et al. |
| 2014/0271940 A1 | 9/2014 | Wurzer et al. |
| 2014/0356420 A1 | 12/2014 | Huang |
| 2015/0064250 A1 | 3/2015 | Ghebre-Sellassie et al. |
| 2015/0126595 A1* | 5/2015 | Smith .................. A61K 31/353 514/454 |
| 2015/0258040 A1 | 9/2015 | Lynch et al. |
| 2015/0297556 A1 | 10/2015 | Smith |
| 2016/0029658 A1 | 2/2016 | Segawa et al. |

(Continued)

FOREIGN PATENT DOCUMENTS

| | | |
|---|---|---|
| CA | 2684562 | 10/2008 |
| CN | 100482657 | 7/2005 |

(Continued)

OTHER PUBLICATIONS

Marriott, Pharmaceutical Compound and Dispensing, Second Edition, 2010, 1-288.*

(Continued)

*Primary Examiner* — Nizal S Chandrakumar
(74) *Attorney, Agent, or Firm* — Sheridan Ross P.C.

(57) ABSTRACT

This disclosure relates to new printable cannabinoid and terpene compositions, and method for making and using the same. Inkjet printer technology is used to dose precise amounts of purified cannabinoids such that a user may select the type of effect desired and in the amount they want. Various methods include inhaling and ingesting through the use of different substrates.

12 Claims, No Drawings

(56) References Cited

U.S. PATENT DOCUMENTS

| | | |
|---|---|---|
| 2016/0081976 A1 | 3/2016 | Bromley |
| 2016/0250270 A1 | 9/2016 | Cooper et al. |
| 2016/0256395 A1 | 9/2016 | De Vries et al. |
| 2016/0279073 A1 | 9/2016 | Donsky et al. |
| 2017/0049754 A1 | 2/2017 | Diederich et al. |
| 2017/0266153 A1 | 9/2017 | Levy et al. |
| 2019/0388384 A1 | 12/2019 | Segal et al. |

FOREIGN PATENT DOCUMENTS

| | | |
|---|---|---|
| CN | 102869356 | 1/2013 |
| CN | 103826621 | 5/2014 |
| GB | 2495118 | 4/2013 |
| WO | 2008024408 A2 | 2/2008 |
| WO | 2011135591 A2 | 11/2011 |
| WO | WO 2014/100231 | 6/2014 |
| WO | WO 2014/159688 | 10/2014 |
| WO | WO 2015/068052 | 5/2015 |
| WO | WO 2015/200049 | 12/2015 |
| WO | WO 2016/109624 | 7/2016 |
| WO | WO 2018/011808 | 1/2018 |

OTHER PUBLICATIONS

Ansel, Pharmaceutical Dosage Forms and Drug Delivery Systems, 1999.*

Chen, "Some of the Parts: Is Marijuana's 'Entourage Effect' Scientifically Valid?" Scientific American, Apr. 20, 2017, retrieved from https://www.scientificamerican.com/article/some-of-the-parts-is-marijuana-rsquo-s-ldquo-entourage-effect-rdquo-scientifically-valid/, 3 pages.

Mosely, "Ebbu Announces Groundbreaking Production Scale Purification Process," Business Wire, Jun. 13, 2016, retrieved from https://www.businesswire.com/news/home/20160613006490/en/Ebbu-Announces-Groundbreaking-Production-Scale-Purification-Process, 2 pages.

Ross et al., "The Volatile Oil Composition of Fresh and Air-Dried Buds of Cannabis sativa," Journal of Natural Products, vol. 59, No. 1, Jan. 1996, pp. 49-51.

McPartland, John M., et al., "Cannabis and Cannabis Extracts: Greater than the Sum of Their Parts?" The Haworth Press, Inc., www.HaworthPress.com, pp. 103-132 (2001).

McPartland, John M., et al., "Side Effects of Pharmaceuticals Not Elicited by Comparable Herbal Medicines: The Case of Tetrahydrocannabinol and Marijuana," Alternative Therapies in Health and Medicine, vol. 5, No. 4, pp. 57-62, (Jul. 1999).

Russo, Ethan B., "Taming THC: potential cannabis synergy and phytocannabinoid-terpenoid entourage effects," British Journal of Pharmacology, www.brjpharmacol.org, vol. 163, pp. 1344-1364 (2011).

Mosely, "Ebbu Announces Groundbreaking Production Scale Purification Process," Business Wire, Jun. 13, 2016, retrieved from www.businesswire.com/news/home/20160613006490/en/Ebbu-Announces-Groundbreaking-Production-Scale-Purification-Process, 2 pages.

Tomic et al., "Antihyperalgesic and Antiedematous Activities of Bisabolol-Oxides-Rich Matricaria Oil in a Rat Model of Inflammation," Phytotherapy Research, vol. 28, 2014, pp. 759-766.

Haibo et al., "Research Progress on Chemical ingredient and Pharmacological activity of Fructus Cannabis," Chinese Journal of Ethnomedicine and Ethnophamacy, vol. 19, No. 8, 2010, pp. 56-57.

Izzo et al., "Inhibitory effect of cannabichromene, a major non-psychotropic cannabinoid extracted from Cannabis sativa, on inflammation-induced hypermotility in mice," British Journal of Pharmacology, vol. 166, 2012, pp. 1444-1460.

Klauke et al., "The cannabinoid CB2 receptor-selective phytocannahinoid beta-cryophyllene exerts analgesic effects in mouse models of inflammatory and neuropathic pain," European Neuropsychopharmacology, vol. 24, 2014, pp. 608-620.

Maione et al., "Non-psychoactive cannabinoids modulate the descending pathway of antinociception in anaesthetized rats through several mechanisms of action," British Journal of Pharmacology, vol. 1662, 2011, pp. 584-596.

Omar et al., "Optimisation and characterisation of marihuana extracts obtained by supercritical fluid extraction and focused ultrasound extraction and retention time locking GC-MS," Journal of Separate Science, vol. 36, 2013, pp. 1397-1404.

Wirth et al., "Anti-Inflammatory Properties of Cannabichromene," Life Sciences, vol. 26, No. 23, 1980, 5 pages.

Wright et al., "Cannabinoid CB2 receptors in the gastrointestinal tract: a regulatory system in states of inflammation," British Journal of Pharmacology, vol. 153, 2008, pp. 263-270.

\* cited by examiner

PRINTABLE CANNABINOID AND TERPENE COMPOSITIONS

CROSS REFERENCE TO RELATED APPLICATIONS

This application is being filed under 35 U.S.C. 371 and is the National Stage of International Application No. PCT/US2016/065455 filed Dec. 7, 2016, which claims priority under 35 U.S.C. 119 to U.S. Provisional Application No. 62/349,932 filed Aug. 2, 2016; 62/354,463 filed Jun. 24, 2016; 62/348,114 filed Jun. 9, 2016; and 62/347,558 filed Jun. 8, 2016; and is a continuation of U.S. application Ser. No. 15/055,499 filed Feb. 26, 2016, which claims priority to U.S. Provisional Application No. 62/264,281 filed Dec. 7, 2015, which are herein incorporated by reference in their entireties.

TECHNICAL FIELD

This disclosure relates to the *cannabis* industry. In particular, this disclosure relates to using inkjet technology to print cannabinoid and/or terpene compositions onto substrates, ink compositions for printing onto substrates, and methods for making and using printed substrates.

BACKGROUND

Inkjet technology is used in most everyday tasks. Inkjet printers are easy to use, precise, and widely available. Most inkjet printers are used in the academic and work environment, printing reports, essays, spreadsheets, etc. However, inkjet technology is not limited to the printing industry.

At a fundamental level, inkjet printers work by propelling droplets of ink onto a substrate. Meaning, inkjet printers are capable of printing a number of different compositions on a number of different surfaces. Printing different "inks" onto different substrates allows for a wide variety of uses in a number of fields, e.g., the medical industry, culinary arts, textiles, etc.

One unique application is the creation of certain inks containing chemical positions. Inkjet printers are capable of quickly processing precise dosages of chemical compositions onto a substrate of choice. One particular area of interest is cannabinoids from *cannabis*.

*Cannabis* is a genus of flowering plants that include the species: *Cannabis sativa*, *Cannabis indica*, and *Cannabis ruderalis*. *Cannabis* has long been used for hemp fibers, seed and seed oils, medicinal purposes, and recreational purposes.

*Cannabis* is composed of 483 known chemical compounds, which include cannabinoids, terpenoids, flavonoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, terpenes, non-cannabinoid phenols, vitamins, pigments, and elements.

Harvesting secondary compounds from a plant of genus *cannabis* typically requires harvesting trichomes. Trichomes contain the largest amounts of secondary compounds, such as cannabinoids, like THC, CBN, CBC, CBGV, CBGVA, CBDV, CBCV, THCV, CBDVA, CBGA, CBCV, CBCVA CBL, CBG, CBD.

Trichomes come from the flowering parts of the *cannabis* plant. The flowering stage varies from about 6 to 22 weeks, depending on the type of *cannabis* plant. *Cannabis indica* plants are generally believed to require shorter flowering times than *Cannabis sativa* plants. During flowering, unpollinated female plants produce buds containing sticky, white resin glands, aka trichomes.

Most extractions of *cannabis* aim to extract cannabinoids, particularly tetrahydrocannabinol (THC). THC has many known effects including relieving pain, treating glaucoma, relieving nausea, and inducing vomiting during cancer treatments. THC's most well-known property is the psychoactive effect that creates the "high" often associated with *cannabis*. However, each cannabinoid has their own effects and properties that make them a compound of interest. Examples include, Cannabigerol (CBG), Cannabigerolic Acid (CBGA), Cannabidiol (CBD), Cannabinol (CBN), Cannabichromene (CBC), Tetrahydrocannabivarin (THCV), Cannabigerovarin (CBGV), and Cannabigerovarinic Acid (CBGVA).

Cannabinoids are difficult to prescribe because people react to cannabinoids differently. Also, most doses of cannabinoids are in fixed amounts, e.g., 5 mg, 25 mg, 100 mg, etc., making it difficult to prescribe. Besides ingestion, the most common method is smoking. Smoking poses a number of difficulties. First, is the unpredictability of the dosage of cannabinoids since most methods involve burning *cannabis*. The same mass of *cannabis* will have different levels of cannabinoids compared to other plants of the same mass because of different species, strains, age, etc. Second, inhaling smoke is not healthy and can pose a number of different health problems.

There exists a need for compositions comprising new combinations of purified cannabinoids for either ingestion or inhalation. There also exists a particular need for compositions providing one or more purified cannabinoids in combination with a purified terpene. Furthermore, there exists a need to provide precise amounts of one or more purified cannabinoids with or without one or more purified terpenes. There exists a need to supply these compounds as layered compositions on inert substrates for either administering orally or via inhalation.

DETAILED DESCRIPTION

Disclosed herein are new printable compositions and ink compositions comprising a purified cannabinoid and/or a purified terpene.

Disclosed herein are new methods for making a cannabinoid and/or terpene composition having precise dosages. In one embodiment, the composition is ingested. In one embodiment, the composition is inhaled.

Disclosed herein are new printable compositions comprising more than one purified cannabinoid and with more than one purified terpene. In one embodiment, the compositions are printed onto a digestible substrate. In one embodiment, the compositions are printed onto a burnable substrate.

Disclosed herein are new methods of printing precise amounts of a purified cannabinoid and/or a purified terpene onto a substrate.

Disclosed herein are new compositions printed with an inkjet printer comprising:
  a purified cannabinoid;
  a purified terpene;
  an excipient;
  a solvent; and
  a substrate.

As used herein, the term "purified" means isolated from the plant (e.g., by using chromatography, distillation, extractions, or similar technique) resulting in a greater than 60% purity. In some embodiments, the "purified" compositions disclosed herein are greater than 70% purity. In some embodiments, the "purified" compositions disclosed herein are greater than 80% purity. In some embodiments, the "purified" compositions disclosed herein are greater than 90% purity.

As used herein, the term "cannabinoid" means an organic substance isolated from a *cannabis* plant acting upon a cannabinoid receptor or a derivative thereof, or a structurally similar substance. Within the context of this disclosure, the term "cannabinoid" includes but is not limited to phytocannabinoids. For example, the term cannabinoid includes cannabinoid ligands such as agonists, partial agonists, inverse agonists, or antagonists, as demonstrated by binding studies and functional assays. In many examples, a cannabinoid can be identified because its chemical name will include the text string "*cannabi*" in the name. Within the context of this disclosure, where reference is made to a particular cannabinoid, each of the acid and/or decarboxylated forms and/or varying forms are contemplated as both single molecules and mixtures.

Examples of cannabinoids within the context of this disclosure include any of the following molecules, their derivatives, salts, or analogs: Tetrahydrocannabinol (THC), Tetrahydrocannabinolic Acid (THCA), Tetrahydrocannabivarin (THCV), Tetrahydrocannabivarin Carboxylic Acid (THCVA), Cannabichromene (CBC), Cannabichromenic Acid (CBCA), Cannabichromevarinic Acid (CBCVA), Cannabivarichromene (CBCV), Cannabichromanon (CBCN), Cannabidiol (CBD), Cannabidiolic Acid (CBDA), Cannabidivarinic Acid (CBDVA), Cannabielsoin (CBE), Cannabidivarin (CBDV), Cannbifuran (CBF), Cannabigerol (CBG), Cannabigerolic Acid (CBGA), Cannabigerovarin (CBGV), Cannabigerovarinic Acid (CBGVA), Cannabicyclol (CBL), Cannabinol (CBN), Cannabinodiol (CBND), Cannabitriol (CBT), and Cannabivarin (CBV). These are merely examples and are not meant to be limiting. As used herein, the term "excipient" means a natural or synthetic substance acting as a filler formulated with other compositions (e.g., active ingredients), such that the compositions are combined in the correct proportions of active ingredients while also achieving a particular volume, mass, or any other measurement.

As used herein, the term "solvent" means a substance that dissolves a solute (a chemically different liquid, solid or gas), resulting in a solution. In one embodiment, a solvent is a liquid. In one embodiment, a solvent is a gas. In one embodiment, a solvent is a solid.

As used herein, the term "substrate" refers to a solid surface. Within the context of this disclosure, a substrate is capable of receiving one or more compositions via deposition, such as printing a composition onto a substrate. The substrate may receive one or more deposits of one or more compositions, forming homogenous layers or heterogeneous layers, optionally having distinct layers of different compositions.

In one embodiment the purified cannabinoid is chosen from Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-C4 (CBD-C4), Cannabidivarinic Acid (CBDVA), Cannabidivarin (CBDV), Cannabidiorcol (CBD-C1), Tetrahydrocannabinolic acid A (THCA-A), Tetrahydrocannabinolic acid B (THCA-B), Tetrahydrocannabinol (THC), Tetrahydrocannabinolic acid C4 (THCA-C4), Tetrahydrocannbinol C4 (THC-C4), Tetrahydrocannabivarinic acid (THCVA), Tetrahydrocannabivarin (THCV), Tetrahydrocannabiorcolic acid (THCA-C1), Tetrahydrocannabiorcol (THC-C1), Delta-7-cis-iso-tetrahydrocannabivarin, Δ8-tetrahydrocannabinolic acid (Δ8-THCA), Δ8-tetrahydrocannabinol (Δ8-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabinolic acid (CBNA), Cannabinol (CBN), Cannabinol methylether (CBNM), Cannabinol-C4 (CBN-C4), Cannabivarin (CBV), Cannabino-C2 (CBN-C2), Cannabiorcol (CBN-C1), Cannabinodiol (CBND), Cannabinodivarin (CBDV), Cannabitriol (CBT), 10-Ethoxy-9-hydroxy-Δ6a-tetrahydrocannabinol, 8,9-Dihydroxy-Δ6a(10a)-tetrahydrocannabinol (8,9-Di-OH-CBT-C5), Cannabitriolvarin (CBTV), Ethoxy-cannabitriolvarin (CBTVE), Dehydrocannabifuran (DCBF), Cannbifuran (CBF), Cannabichromanon (CBCN), Cannabicitran (CBT), 10-Oxo-Δ6a(10a)-tetrahydrocannabinol (OTHC), Δ9-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Isocanabinoids, Epigallocatechin gallate, Dodeca-2E, 4E,8Z,10Z-tetraenoic acid isobutylamide, or Dodeca-2E, 4E-dienoic acid isobutylamide.

In one embodiment the purified cannabinoid is chosen from THC, CBD, CBC, CBG, or THCV.

As used herein, the term "THC" refers to Tetrahydrocannabinol, which has the following structural formula:

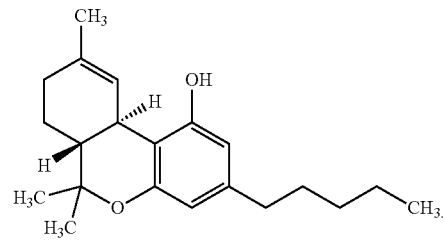 [SMILES: CCCCCc1cc(O)c2c(c1)OC(C)(C)[C@@H]1CCC(C)=C[C@@H]21]

THC is often characterized as having many medical effects including relieving pain, treating glaucoma, relieving nausea, and inducing vomiting during cancer treatments. THC is often noted for having psychoactive effects.

As used herein, the term CBD refers to Cannabidiol, which has the following structural formula:

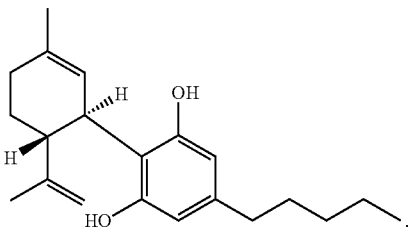 [SMILES: C=C(C)[C@@H]1CCC(C)=C[C@H]1c1c(O)cc(CCCCC)cc1O]

CBD is noted for being the second most abundant cannabinoid produced in plants of genus *cannabis*. CBD is often characterized as having many medical applications including, but not limited to, inhibiting cancer cells, suppressing inflammation, and suppressing seizures. CBD is often described as not having psychoactive effects.

As used herein, the term "CBC" refers to Cannabichromene, which has the following structural formula:

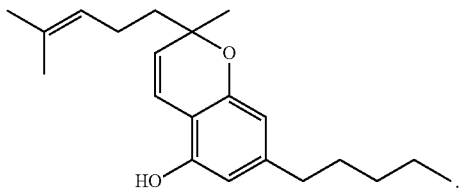 [SMILES: CCCCCc1cc(O)c2c(c1)OC(C)(CCC=C(C)C)C=C2]

CBC is often regarded for its anti-inflammatory and antiviral properties. CBC has two known stereoisomers, either or both of which are disclosed herein. CBC boils at 220 degree Celsius (428 degree Fahrenheit).

As used herein, the term "CBG" refers to Cannabigerol, which has the following structural formula:

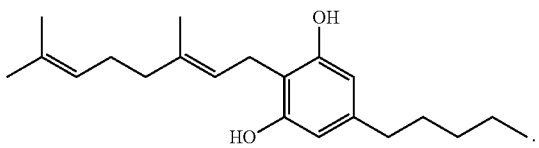 [SMILES: CCCCCc1cc(O)c(C/C=C(\C)CCC=C(C)C)c(O)c1]

Decarboxylating CBGA with heat, light, etc. forms CBG.

As used herein, the term "THCV" refers to Tetrahydrocannabivarin, THV, THCv, THC-V, etc., which has the following structural formula:

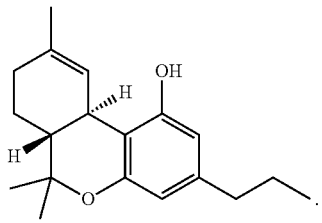 [SMILES: CCCc1cc(O)c2c(c1)OC(C)(C)[C@@H]1CCC(C)=C[C@@H]21]

THCV is a known analog of THC, wherein THCV has a propyl side chain where THC has a pentyl side chain. THCV is reported to suppress appetite, regulate blood sugar, and ease anxiety.

As used herein, the term "terpene" means an organic compound built on an isoprenoid structural scaffold or produced by combining isoprene units. Often, terpene molecules found in plants are aromatic molecules, having a distinctive fragrance, such as alpha-pinene, which is often said to smell like pine.

In one embodiment the purified terpene is chosen from 7,8-dihydroionone, Acetanisole, Acetic Acid, Acetyl Cedrene, Anethole, Anisole, Benzaldehyde, Bergamotene (α-cis-Bergamotene) (α-trans-Bergamotene), α-Bisabolol, Bornyl acetate, Borneol, Butanoic, Butyric Acid, Cadinene (α-Cadinene) (γ-Cadinene), Cafestol, Caffeic acid, Camphene, Camphor, Capsaicin, Carene (Δ-3-Carene), Carotene, Carvacrol, Carvone, Dextro-Carvone, Laevo-Carvone, Caryophyllene (β-Caryophyllene), Caryophyllene oxide, Castoreum Absolute, Cedrene (α-Cedrene) (β-Cedrene), Cedrene Epoxide (α-Cedrene Epoxide), Cedrol, Cembrene, Chlorogenic Acid, Cinnamaldehyde (α-amyl-Cinnamaldehyde) (α-hexyl-Cinnamaldehyde), Cinnamic Acid, Cinnamyl Alcohol, Citronellal, Citronellol, Cryptone, Curcumene (α-Curcumene) (γ-Curcumene), D-Limonene, Decanal, Dehydrovomifoliol, Diallyl Disulfide, Dihydroactinidiolide, Dimethyl Disulfide, Eicosane/Icosane, Elemene (β-Elemene), Estragole, Ethyl acetate, Ethyl Cinnamate, Ethyl maltol, Eucalyptol, Eudesmol (α-Eudesmol) (β-Eudesmol) (γ-Eudesmol), Eugenol, Euphol, Farnesene, Farnesol, Fenchol (β-Fenchol), Fenchone, Geraniol, Geranyl acetate, Germacrenes, Germacrene B, Guaia-1(10),11-diene, Guaiol, Guaiacol, Guaiene (α-Guaiene), Gurjunene (α-Gurjunene), Herniarin, Hexanaldehyde, Hexanoic Acid, Humulene (α-Humulene) (β-Humulene), Ionol (3-oxo-α-ionol) (β-Ionol), Ionone (α-Ionone) (β-Ionone), Ipsdienol, Isoamyl acetate, Isoamyl Alcohol, Isoamyl Formate, Isoborneol, Isomyrcenol, Isopulegol, Isovaleric Acid, Isoprene, Kahweol, Lavandulol, Limonene, γ-Linolenic Acid, Linalool, Longifolene, α-Longipinene, Lycopene, Menthol, Methyl butyrate, 3-Mercapto-2-Methylpentanal, Mercaptan/Thiols, β-Mercaptoethanol, Mercaptoacetic Acid, Allyl Mercaptan, Benzyl Mercaptan, Butyl Mercaptan, Ethyl Mercaptan, Methyl Mercaptan, Furfuryl Mercaptan, Ethylene Mercaptan, Propyl Mercaptan, Thenyl Mercaptan, Methyl Salicylate, Methylbutenol, Methyl-2-Methylvalerate, Methyl Thiobutyrate, Myrcene (β-Myrcene), γ-Muurolene, Nepetalactone, Nerol, Nerolidol, Neryl acetate, Nonanaldehyde, Nonanoic Acid, Ocimene, Octanal, Octanoic Acid, P-cymene, Pentyl butyrate, Phellandrene, Phenylacetaldehyde, Phenylethanethiol, Phenylacetic Acid, Phytol, α-Pinene, β-Pinene, Propanethiol, Pristimerin, Pulegone, Quercetin, Retinol, Rutin, Sabinene, Sabinene Hydrate, cis-Sabinene Hydrate, trans-Sabinene Hydrate, Safranal, α-Selinene, α-Sinensal, β-Sinensal, β-Sitosterol, Squalene, Taxadiene, Terpin hydrate, Terpineol, Terpine-4-ol, α-Terpineol, α-Terpinene, γ-Terpinene, Terpinolene, Thiophenol, Thujone, Thymol, α-Tocopherol, Tonka Undecanone, Undecanal, Valencene, Valeraldehyde/Pentanal, Verdoxan, α-Ylangene, Umbelliferone, Valencene or Vanillin.

In one embodiment the purified terpene is chosen from Pulegone, α-Humulene, α-Terpineol, Menthol, Laevo-Carvone, Caryophyllene-oxide, Borneol, Valencene, Guaiacol, β-Eudesmol, α-Bisabolol, Camphene, D-Limonene, Linalool, Terpineol-4-ol, Camphor, α-Pinene, β-Pinene, Terpinolene, Myrcene (β-Myrcene), β-Caryophyllene, Eucalyptol, p-Cymene, Fenchol (β-Fenchol), α-Cedrene, β-Eudesmol, Sabinene, Citronellal, Geraniol, Guaiol, Isoborneol, Elemene (β-Elemene), Bornyl acetate, Carene (Δ-3-Carene), Cedrol, Phytol, and Nerolidol.

In one embodiment, the compositions disclosed herein comprise a terpene chosen from linalool, humulene, or β-Pinene.

In one embodiment, the compositions disclosed herein comprise THC and linalool.

As used herein, the term "pulegone" refers to a cyclic monoterpene with the following structural formula:

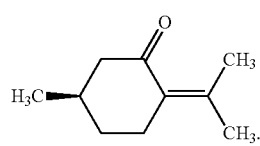

Pulegone is often characterized as having a minty-camphor odor and flavor that is used in the candy industry. Pulegone is an acetylcholinesterase inhibitor. Thus, it stops the action of the protein that destroys acetylcholine, which is used by the brain to store memories. It may counteract THC's activity, which leads to low acetylcholine levels.

As used herein, the term Humulene refers to either or both the α-Humulene and/or the β-Humulene isomers as pure forms or mixtures in any form. They are monocyclic sesquiterpene with an 11-membered ring. α-Humulene refers to the following structural formula:

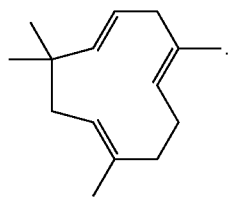

α-Humulene (obsolete name: α-Caryophyllene) is often characterized as having an aroma that has been described as bitter, medium woody, and hoppy. α-Humulene has shown anti-inflammatory properties. Humulene is one of the essential oils made in the flowering cone of the hops plant *Humulus lupulus*. The concentration of humulene varies among different varieties of the plant but can be up to 40% of the essential oil of noble hops.

As used herein, the term "α-Terpineol" refers to a cyclic monoterpene alcohol with the following structural formula:

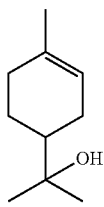

α-Terpineol is often characterized as having a lilac, citrus or apple blossom to lime odor. It is used extensively in the perfume industry.

As used herein, the term "menthol" refers to a cyclohexane with the following structural formula:

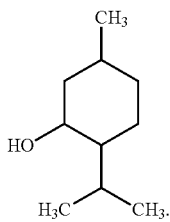

Menthol is often characterized as having a very strong, cooling, mentholic, minty, peppermint aroma and flavor. It is obtained from cornmint, peppermint or other mint oils. Menthol has local anesthetic and counterirritant qualities, and it is widely used to relieve minor throat irritation. Menthol also acts as a weak kappa opioid receptor agonist. Menthol is responsible for the well-known cooling sensation it provokes when inhaled, eaten, or applied to the skin. In this sense, it is similar to capsaicin, the chemical responsible for the spiciness of hot chilies (which stimulates heat sensors, also without causing an actual change in temperature).

As used herein, the term "laevo-carvone" refers to the R-(−) enantiomer of carvone with the following structural formula:

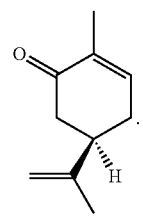

Laevo-Carvone is often characterized as having a sweet, minty, herbaceous, spearmint odor. It is found in spearmint and kuromoji oils. It is used extensively in chewing gums and flavor oils such as spearmint, but is also used in spice and floral fragrances for air fresheners, perfumes, shampoos, deodorants, body wash, laundry detergents, cosmetics and toothpaste.

As used herein, the term "caryophyllene oxide" refers a compound with the following structural formula:

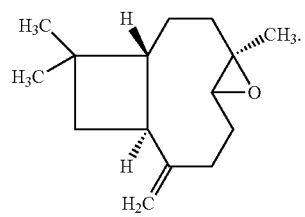 [SMILES: C=C1CCC2O[C@]2(C)CC[C@@H]2[C@@H]1CC2(C)C]

Caryophyllene oxide is often characterized as having a lemon balm odor. It has shown some effectiveness as an insecticidal/antifeedant and as broad-spectrum antifungal in plant defense. Caryophyllene oxide has the distinction of being the main component responsible for *cannabis* identification by drug-sniffing dogs.

As used herein, "α-Bisabolol" refers to a monocyclic sesquiterpene alcohol with the following structural formula:

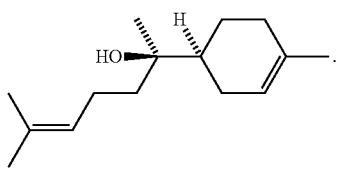 [SMILES: CC(C)=CCC[C@@](C)(O)[C@@H]1CC=C(C)CC1]

α-Bisabolol is often characterized as having a weak, tangy, fresh and clean, citrus, floral, sweet aroma with a peppery note, and is used in various fragrances. It is the primary constituent (up to 50%) of the essential oil from German chamomile. It has shown anti-aging, anti-irritant, anti-inflammatory, antimicrobial, analgesic, antibiotic and anticancer activities.

As used herein, the term "borneol" refers to a compound having the following structural formula:

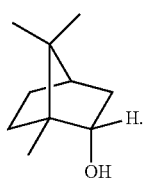

Borneol is often characterized as having a smell much like the menthol aroma of camphor and is easily converted into it. In Chinese medicine, herbs containing borneol are recommended for fatigue and overstress. Borneol is considered a "calming sedative" in Chinese medicine. It is directed for fatigue, recovery from illness and stress. It is found in small quantities in many essential oils. Commercially it is derived from Artemisia plants such as wormwood and some species of cinnamon.

As used herein, the term "valencene" refers to a compound of the following structural formula:

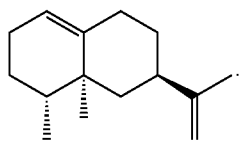

Valencene is often characterized as being an aroma component of citrus fruit and citrus derived odorants.

As used herein, the term "guaiacol" refers to a compound of the following structural formula:

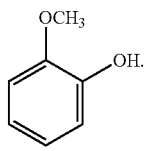

Guaiacol is often characterized for its yellowish appearance and for being an aromatic oil.

As used herein, the term "β-Eudesmol" refers to a compound with the following structural formula:

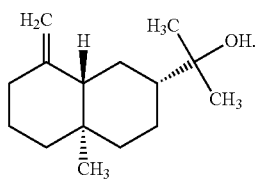 [SMILES: C=C1CCC[C@]2(C)CC[C@@H](C(C)(C)O)C[C@@H]12]

β-Eudesmol is often characterized as having a sweet, green, woody, yuzu-like aroma. It has shown some antioxidant, antimicrobial and anti-wood-decay fungal activities.

As used herein, the term "camphene" refers to a bicyclic monoterpene having the following structural formula:

Camphene is often characterized as having a pungent, herbal, fir needle smell. Its odor has often been described as a camphoraceous, cooling, piney and woody with terpy nuances. It has citrus and green minty and green spicy notes. Camphene is used in fragrances and food additives. It is a minor constituent of many essential oils such as turpentine, cypress oil, camphor oil, citronella oil, neroli, ginger oil, and valerian.

As used herein, the term "D-Limonene" refers to a compound of the structural formula:

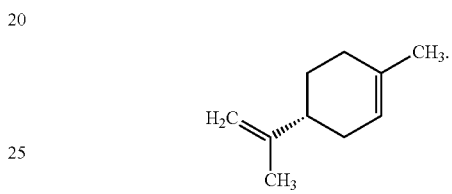

D-Limonene is often characterized as being a major component of oil from citrus rind and has a strong orange smell.

As used herein, the term "linalool" refers to a terpene alcohol that has the following structural formula:

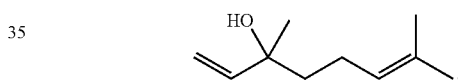

Linalool is being tested for treatment of several types of cancer. It is also a component of several sedating essential oils including lavender oil, which is believed to possess antianxiety and sedative properties. In addition to being a compound that counters anxiety and mediates stress, linalool is a strong anticonvulsant, and it also amplifies serotonin-receptor transmission, conferring an antidepressant effect. Applied topically, linalool can heal acne and skin burns without scarring. Strains that are high in linalool may be particularly beneficial for patients who experience insomnia due to their sedating effects.

As used herein, the term "terpinen-4-ol" refers to the isomer of terpineol that has the following structural formula:

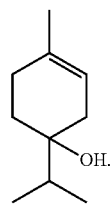

Terpinen-4-ol is often characterized as having a pleasantly herbaceous, peppery, woody odor and is used in commercial fragrances. Terpinen-4-ol is used in fragrances for spice types. It is considered the primary active ingredient of tea tree oil. It is the compound of highest concentration in the essential oil of nutmeg. It also occurs in oil of cypress, juniper berry, Ceylon cardamom, marjoram, thyme, and a few others. It has been shown to act as an AChE inhibitor and as an antibiotic.

As used herein, the term "camphor" refers to a compound with the following structural formula:

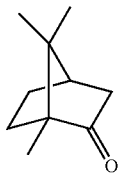

Camphor is often characterized as having a strong, penetrating, persistent odor. It is used as a flavor and fragrance agent in chewing gum and hard candy.

As used herein, the term "α-Pinene" refers to a bicyclic monoterpene with the following structural formula:

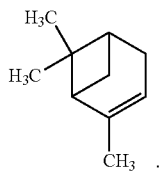

α-Pinene is often associated with the familiar odor associated with pine trees and their resins. It is a major component in turpentine and is found in many other plant essential oils in noticeable amounts including rosemary, sage, eucalyptus and many others.

As used herein, the term "β-Pinene" refers to a monoterpene with the following structural formula:

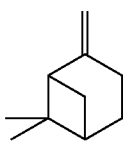

β-Pinene is often characterized as having a woody-green pine-like smell. β-Pinene is one of the most abundant compounds released by forest trees. It is one of the two isomers of pinene (the other being α-Pinene) and it shares similar properties.

As used herein, the term "terpinolene" refers to a cyclic monoterpene with an isoprene group that has the following structural formula:

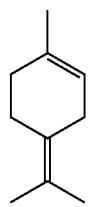

Terpinolene is often characterized as having a medium strength, herbal aroma that has been described as fresh, woody, sweet and piney with a hint of citrus. Its flavor is a sweet, woody, terpy, lemon and lime-like with a slight herbal and floral nuance. It is used as a flavor and fragrance agent. Terpinolene is also known as "δ-Terpinene".

As used herein, the term "Myrcene (β-Myrcene)" refers to a monoterpene with the following structural formula:

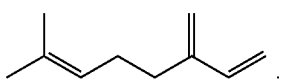

Myrcene is often characterized as the most prevalent terpene found in most varieties of *cannabis* but it is not found in hemp. It is present in significant concentrations in *cannabis* resin itself. It is also found in mango, hops, lemon grass, East Indian bay tree, and verbena. Because of its appealing fragrance, myrcene is used extensively in the perfume industry.

As used herein, the term "β-Caryophyllene" refers to a bicyclic sesquiterpene with the following structural formula:

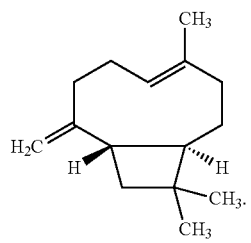

β-Caryophyllene is often characterized as having a sweet, woody and dry clove odor and has a peppery, spicy with camphor and astringent citrus backgrounds. It is a major terpene found in black pepper, clove and cotton. It is often found in smaller percentages in many other green, leafy vegetables, herbs, and spices. Caryophyllene contributes to black pepper's spiciness. Caryophyllene oil is also used industrially to enhance tobacco flavor.

As used herein, the term "Eucalyptol" refers to a cyclic ether and monoterpenoid that has the following structural formula:

Eucalyptol, also referred to as "1,8-Cineole," is often characterized as having a camphor-minty odor of eucalyptus. In fact, it is the main ingredient in oil of eucalyptus. It is also found in other fragrant plants.

As used herein, the term "p-cymene" refers to a compound with the following structural formula:

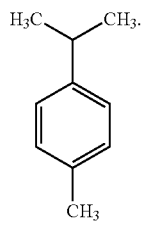

p-Cymene is often characterized as having a musty tang of terpenes with an orange to carrot odor, although synthetic p-Cymene can have a turpentine-like odor. p-Cymene is a constituent of a number of essential oils, most commonly the oils of cumin and thyme.

As used herein, the term "Fenchol (β-Fenchol)" refers to the isomer of borneol with the following structural formula:

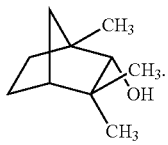

Fenchol (β-Fenchol) is often characterized as having the scent of basil.

As used herein, the term "nerolidol" refers to a sesquiterpene with the chemical formula $C_{15}H_{26}O$. Nerolidol can exist in either of the cis- or trans-isomers. The trans-isomer has the following structural formula:

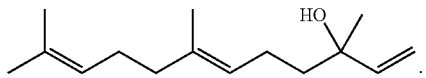 [SMILES: C=CC(C)(O)CC/C=C(\C)CCC=C(C)C]

The cis-isomer has the following structural formula:

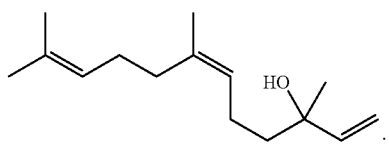 [SMILES: C=CC(C)(O)CC/C=C(/C)CCC=C(C)C]

Within the context of this disclosure, the term "nerolidol" means either or both of the cis- and/or trans-isomers, including mixtures in any proportion. Nerolidol is often characterized as having a mild, delicate odor that is floral, apple, rose, green and citrus-like with woody, waxy nuances. It can be found in ginger, niaouli and citronella. It is present as a low-level component in orange and other citrus peels. It is used as a flavor and fragrance agent. Its flavor has been described as green, floral and woody with fruity-citrus and melon nuances.

As used herein, the term "α-Cedrene" refers to a compound having the following structural formula:

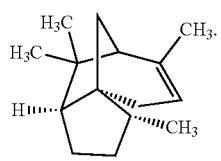

α-Cedrene is often characterized as having a medium strength, woody, sweet, fresh aroma of cedar. It is used in bakery items, sherbet and sorbet. It is a major component in the essential oil of cedar.

As used herein, the term "sabinene" refers to a bicyclic monoterpene that has the following structural formula enantiomers:

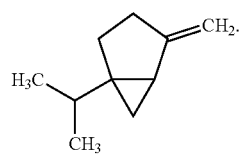

Sabinene is often characterized as having a medium strength, warm, oily-peppery, woody, herbaceous, and spicy pine odor with citrus notes. As a flavoring it is oily, citrus and tropical fruity. It is found in oak trees, tea tree oil, black pepper and is a major constituent of carrot seed oil.

As used herein, the term "citronellal" refers to a monoterpenoid that has the following structural formula:

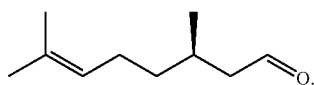

Citronellal is a major component, making up to 80% of the leaf oil from Kaffir lime leaves and is the compound responsible for its characteristic lime aroma.

As used herein, the term "geraniol" refers to a monoterpenoid that has the following structural formula:

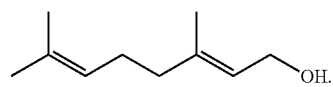

Geraniol is often characterized as having a medium strength, floral, sweet, rosy, fruity odor with citrus to citronella-like odor nuances. Its flavor is floral, rosy, waxy and perfume-like with a fruity peach-like nuance. It is used as a flavor and fragrance agent. It is used in flavors such as peach, raspberry, grapefruit, red apple, plum, lime, orange, lemon, watermelon, pineapple, and blueberry. It is also used for cosmetic as a perfuming agent. Geraniol is a natural antioxidant.

As used herein, the term "Carene (Δ-3-Carene)" refers to a bicyclic monoterpene that has the following structural formula:

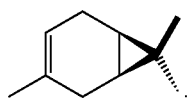

Carene differs from camphor and camphene by having a double bound within the ring structure. Carene is often characterized as having a medium strength, sweet, pungent citrus odor. It is a constituent of pine and cedar resin but is found in many other plants including rosemary.

As used herein, the term "Guaiol" refers to a compound of the following structural formula:

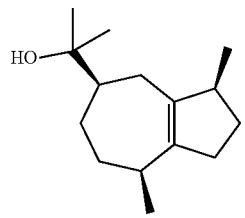

Guaiol can often be found in the oil of guaiacum and cypress pine. It can yield a deep purple color when reacted with electrophilic bromine reagents.

As used herein, the term "isoborneol" refers to an isomer of borneol with the alcohol group in a different position with the following structural formula:

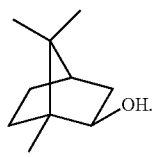

Isoborneol is often characterized as having a camphoraceous, sweet & musty, India ink-like aroma. It has shown antioxidant, anti-inflammatory and some limited antimicrobial properties. It is used as a flavor and fragrance agent for beverages, ice cream, candy, baked goods, and chewing gum.

As used herein, the term Elemene (β-Elemene) refers to a cyclic sesquiterpene that has the following structural formula:

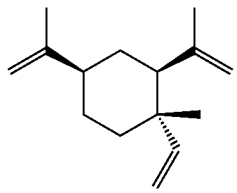

Elemene is often characterized as having a medium strength, sweet aroma. The parenteral form of β-elemene is isolated from *Rhizoma zedoariae*, a type of ginger, although it is a volatile terpene found in botanicals such as celery, mint, and it is prevalent in a variety of medicinal plants.

As used herein, the term "bornyl acetate" refers to an acetate that has a borneol group with the following structural formula:

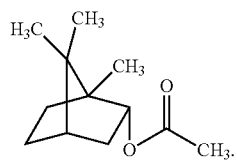

Bornyl acetate is often characterized as having a pine, camphoraceous, herbal, and balsamic odor.

As used herein, the term "cedrol" refers to a sesquiterpene alcohol having the following structural formula:

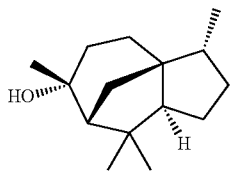

Cedrol is often characterized as having a very faint aroma that is sweet, soft, dry and cedar woody. Cedrol is a major component of cedar wood oil. It is found in the essential oil of conifers, especially in cypress and juniper. It has also been identified in *Origanum onites*, a plant related to oregano.

As used herein, the term "phytol" refers to diterpene alcohol with the following structural formula:

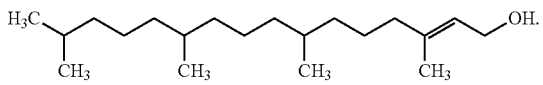

Phytol is often characterized having a mild, light floral, balsamic, green jasmine, green tea type of aroma. It's been shown to prevent Vitamin A teratogenesis.

In one embodiment, the substrate used within the claimed invention is a water-soluble substrate. As used herein, the term "water soluble substrate" means a substrate dissolvable in water or in an aqueous substance without affecting the active ingredients. Examples for this disclosure include, but are limited to, paper, sugar sheets, and dissolvable films. In one embodiment the substrate is an inert substrate.

In one embodiment, the substrate used within the claimed invention is an inert substrate. As used herein, the term "inert substrate" refers to a substrate that is chemically nonreactive. Examples of inert substrates within the context of this disclosure include, but are not limited to, sintered metals, sintered glass, controlled porous glass, carbon nanotubes, and zeolites. In one embodiment, the inert substrate is heatproof. In one embodiment the inert substrate is stable at elevated temperatures.

As used herein, the term "stable" means nonreactive to an applied stimulus. For example, a substrate maintaining its shape without any warping, bending, cracking; not combusting; not oxidizing; and/or not undergoing any chemical or other physical change during the period that the stimulus is applied. In one embodiment, the stimulus is heat. In one embodiment, the stimulus is movement.

In one embodiment, "elevated temperatures" means temperatures of about 100-200 C. In one embodiment, "elevated temperature" means temperatures of about 200-300 C. In one embodiment, "elevated temperature" means temperatures of about 300-500 C. In one embodiment, "elevated temperature" means temperatures of about 500-1000 C.

Disclosed herein are new printable ink compositions comprising:
 a purified cannabinoid;
 a purified terpene;
 an excipient; and
 a solvent.

Disclosed herein are new methods of making an ingestible cannabinoid composition comprising:
 printing a composition comprising a purified cannabinoid onto a substrate.

As used herein, the term "ingestible cannabinoid" means a cannabinoid consumable by a person by the traditional oral route. In one embodiment, an ingestible cannabinoid is an edible. In one embodiment, an ingestible cannabinoid is a tea. In one embodiment, an ingestible cannabinoid is an oil.

Disclosed here is a new method of making consistently dosed printed cannabinoid formulations comprising:
 preparing a bulk standard printable ink composition comprising a purified cannabinoid, a purified terpene, an excipient, and a solvent; and
 printing the printable ink composition onto a plurality of substrates.

As used herein, the term "consistently dosed" means to have substantially the same amount of active ingredient or active ingredients dispersed on each substrate. In one embodiment, "consistently dosed" means the difference between doses having substantially the same amount of active ingredient is +/−0.01 mg up to 5 mg. In one embodiment, the difference between doses having substantially the same amount of active ingredient is +/−0.05 mg up to 1 mg. In one embodiment, the difference between doses having substantially the same amount of active ingredient is +/−0.1 mg up to 2.5 mg.

As used herein, the term "bulk standard" means a large scale portion of ink, having a relatively large amount of active ingredient or active ingredients and/or non-active ingredient, providing a uniformly consistent ratio of active ingredient to mass and/or volume.

As used herein, the term "plurality of substrates" means more than one substrate of any type or combinations of different substrates.

Disclosed herein is a new method of consistently dosing cannabinoids in the vapor phase comprising:
 preparing a printable ink composition comprising a purified cannabinoid, an excipient, and a solvent;
 printing the printable ink composition onto a plurality of substrates; and
 heating one or more substrates to a vaporization temperature of the purified cannabinoid.

As used herein, the term "vapor phase" means the gas phase of a substance.

As used herein, the term "vaporization temperature" means the temperature at which a substance begins to enter the gas phase.

Disclosed herein is a new method of consistently dosing terpenes in the vapor phase comprising:
 preparing a printable ink composition comprising a purified terpene, an excipient, and a solvent; and
 printing the printable ink composition onto a plurality of substrates; and
 heating one or more substrates to the vaporization temperature of the purified terpene.

In one embodiment, method of consistently dosing a cannabinoid and/or a terpene via the vapor phase comprises:
 preparing a printable ink composition comprising a purified cannabinoid, a purified terpene, an excipient, and a solvent;
 printing the printable ink composition onto a plurality of substrates; and
 heating one or more substrates to the vaporization temperature of the purified cannabinoid and purified terpene.

In one embodiment, the method of consistently dosing a cannabinoid and/or terpene comprises of:
 printing a first layer of a compound chosen from a purified cannabinoid or a purified terpene onto a substrate; and
 printing a second layer of a compound chosen from a purified cannabinoid or a purified terpene onto the first layer.

As used herein, the terms "layer" means a single thickness of a substance covering a surface. Within the context of this disclosure, a layer refers to an ink composition printed onto a substrate in a single thickness. Then, either the same or different ink composition is printed on top of the previous layer in either the same or different thickness creating varying layers of compositions.

In one embodiment, the methods disclosed herein comprise printing onto the second layer, a third layer of a compound chosen from a purified cannabinoid, flavonoid, or a purified terpene.

As used herein, the term "flavonoid" means compound having 15 carbon atoms, with two phenyl rings, and at least one heterocyclic ring.

Disclosed herein is a new composition printed with an inkjet printer comprising:
 a cannabinoid;
 a terpene;
 an excipient;
 a solvent; and
 a substrate.

In one embodiment the methods disclosed herein comprise:
 printing a first layer of a compound chosen from a purified cannabinoid or a purified terpene onto a substrate; and
 printing a second layer of a compound chosen from a purified cannabinoid, an absorption enhancer, or a purified terpene onto the first layer.

As used herein, the term "absorption enhancer" means a substance helping the active ingredient or active ingredients be taken in the body more readily. Within the context of this invention, the term "absorption enhancer" includes compounds for oral and/or transmucosal absorption enhancement. Some examples of absorption enhancers are described in "Absorption Enhancers: Applications and Advances," The AAPS Journal, Vol. 14, No. 1, March 2012.

In one embodiment the disclosed method comprises printing a third layer of a compound chosen from a purified cannabinoid, flavonoid, an absorption enhancer, or a purified terpene onto the second layer.

Disclosed herein is a new method of making an ingestible cannabinoid composition comprising:
 printing a cannabinoid extract onto a substrate.

As used herein, the term "cannabinoid extract" means a solution where a solvent was used to separate the active ingredient from the *cannabis* plant. In one embodiment, the active ingredient is a secondary compound. In one embodiment, the secondary compound is a cannabinoid. In one embodiment, the cannabinoid is THC. In one embodiment, the cannabinoid is CBC. In one embodiment, the cannabinoid is CBD. In one embodiment, the cannabinoid is CBG. In one embodiment, the cannabinoid is THCV.

Although the disclosed invention has been described with reference to various exemplary embodiments, it is to be understood that these embodiments are merely illustrative of the principles and applications of the present invention. Those having skill in the art would recognize that various modifications to the exemplary embodiments may be made, without departing from the scope of the invention.

Moreover, it should be understood that various features and/or characteristics of differing embodiments herein might be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

Finally, it is noted that, as used in this specification and the appended claims, the singular forms "a," "an," and "the," include plural referents unless expressly and unequivocally limited to one referent, and vice versa. As used herein, the term "include" or "comprising" and its grammatical variants are intended to be non-limiting, such that recitation of an item or items is not to the exclusion of other like items that can be substituted or added to the recited item(s).

EXAMPLES

Example 1

To prepare a bulk standard of ink, purified THC, purified linalool, glycerin, ethanol, polyvinylpyrrolidone, and water are combined.

Purified THC was used at ≥50% purity as determined by HPLC.

Purified linalool was used at ≥60% purity as determined by HPLC.

70 mL of purified THC and 3.0 mL of purified linalool are combined with 7.0 mL of glycerin, 20 mL of ethanol, and 100 mg of polyvinylpyrrolidone to make an ink composition comprising of 70% THC by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available inkjet printer. The composition was then printed onto water-soluble paper in a single layer in a continuous pattern such that substantially all of the printable area was covered. The paper was then divided into individual doses having 10 mg+/−1 mg of THC per individual dose.

Example 2

To prepare a bulk standard of ink, purified THC, purified linalool, glycerin, ethanol, polyvinylpyrrolidone, and water are combined.

Purified THC is used at ≥60% purity as determined by HPLC.

Purified linalool is used at ≥70% purity as determined by HPLC.

70 mL of purified THC and 3.0 mL of purified linalool are combined with 7.0 mL of glycerin, 20 mL of ethanol, and 100 mg of polyvinylpyrrolidone to make an ink composition comprising of 70% THC by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available inkjet printer. The composition was then printed onto water-soluble paper in a single layer in a continuous pattern such that substantially all of the printable area was covered. The paper was then divided into individual doses having 100 mg+/−5 mg of THC per individual dose.

Example 3

To prepare a bulk standard of ink, purified THC, purified linalool, glycerin, ethanol, polyvinylpyrrolidone, and water are combined.

Purified THC was used at ≥70% purity as determined by HPLC.

Purified linalool was used at ≥80% purity as determined by HPLC.

70 mL of purified THC and 3.0 mL of purified linalool are combined with 7.0 mL of glycerin, 20 mL of ethanol, and 100 mg of polyvinylpyrrolidone to make an ink composition comprising of 70% THC by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 1 mg+/−0.01 mg of THC per individual dose.

Example 4

To prepare a bulk standard of ink, purified THC, purified humulene, glycerin, ethanol, polyvinylpyrrolidone, and water are combined.

Purified THC was used at ≥50% purity as determined by HPLC.

Purified humulene was used at ≥60% purity as determined by HPLC.

70 mL of purified THC and 3.0 mL of purified humulene are combined with 7.0 mL of glycerin, 20 mL of ethanol, and 100 mg of polyvinylpyrrolidone to make an ink composition comprising of 70% THC by weight and 3% humulene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 10 mg+/−1 mg of THC per individual dose.

Example 5

To prepare a bulk standard of ink, purified THC, purified humulene, glycerin, ethanol, polyvinylpyrrolidone, and water are combined.

Purified THC is used at ≥60% purity as determined by HPLC.

Purified humulene is used at ≥70% purity as determined by HPLC.

70 mL of purified THC and 3.0 mL of purified humulene are combined with 7.0 mL of glycerin, 20 mL of ethanol, and 100 mg of polyvinylpyrrolidone to make an ink composition comprising of 70% THC by weight and 3% humulene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 100 mg+/−5 mg of THC per individual dose.

Example 6

To prepare a bulk standard of ink, purified THC, purified humulene, glycerin, ethanol, polyvinylpyrrolidone, and water are combined.

Purified THC was used at ≥70% purity as determined by HPLC.

Purified humulene was used at ≥80% purity as determined by HPLC.

70 mL of purified THC and 3.0 mL of purified humulene are combined with 7.0 mL of glycerin, 20 mL of ethanol, and 100 mg of polyvinylpyrrolidone to make an ink composition comprising of 70% THC by weight and 3% humulene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 1 mg+/−0.01 mg of THC per individual dose.

Example 7

To prepare a bulk standard of ink, purified CBG, purified linalool, glycerin, ethanol, polyvinylpyrrolidone, and water are combined.

Purified CBG was used at ≥50% purity as determined by HPLC.

Purified linalool was used at ≥60% purity as determined by HPLC.

70 mL of purified CBG and 3.0 mL of purified linalool are combined with 7.0 mL of glycerin, 20 mL of ethanol, and 100 mg of polyvinylpyrrolidone to make an ink composition comprising of 70% CBG by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 10 mg+/−1 mg of CBG per individual dose.

Example 8

To prepare a bulk standard of ink, purified CBG, purified linalool, glycerin, ethanol, polyvinylpyrrolidone, and water are combined.

Purified CBG is used at ≥60% purity as determined by HPLC.

Purified linalool is used at ≥70% purity as determined by HPLC.

70 mL of purified CBG and 3.0 mL of purified linalool are combined with 7.0 mL of glycerin, 20 mL of ethanol, and 100 mg of polyvinylpyrrolidone to make an ink composition comprising of 70% CBG by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 100 mg+/−5 mg of CBG per individual dose.

Example 9

To prepare a bulk standard of ink, purified CBG, purified linalool, glycerin, ethanol, polyvinylpyrrolidone, and water are combined.

Purified CBG was used at ≥70% purity as determined by HPLC.

Purified linalool was used at ≥80% purity as determined by HPLC.

70 mL of purified CBG and 3.0 mL of purified linalool are combined with 7.0 mL of glycerin, 20 mL of ethanol, and 100 mg of polyvinylpyrrolidone to make an ink composition comprising of 70% CBG by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 1 mg+/−0.01 mg of CBG per individual dose.

Example 10

To prepare a bulk standard of ink, purified CBC, purified linalool, glycerin, ethanol, polyvinylpyrrolidone, and water are combined.

Purified CBC was used at ≥50% purity as determined by HPLC.

Purified linalool was used at ≥60% purity as determined by HPLC.

70 mL of purified CBC and 3.0 mL of purified linalool are combined with 7.0 mL of glycerin, 20 mL of ethanol, and 100 mg of polyvinylpyrrolidone to make an ink composition comprising of 70% CBC by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 10 mg+/−1 mg of CBC per individual dose.

Example 11

To prepare a bulk standard of ink, purified CBC, purified linalool, glycerin, ethanol, polyvinylpyrrolidone, and water are combined.

Purified CBC is used at ≥60% purity as determined by HPLC.

Purified linalool is used at ≥70% purity as determined by HPLC.

70 mL of purified CBC and 3.0 mL of purified linalool are combined with 7.0 mL of glycerin, 20 mL of ethanol, and 100 mg of polyvinylpyrrolidone to make an ink composition comprising of 70% THC by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 100 mg+/−5 mg of CBC per individual dose.

Example 12

To prepare a bulk standard of ink, purified CBC, purified linalool, glycerin, ethanol, polyvinylpyrrolidone, and water are combined.

Purified CBC was used at ≥70% purity as determined by HPLC.

Purified linalool was used at ≥80% purity as determined by HPLC.

70 mL of purified CBC and 3.0 mL of purified linalool are combined with 7.0 mL of glycerin, 20 mL of ethanol, and 100 mg of polyvinylpyrrolidone to make an ink composition comprising og 70% CBC by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 1 mg+/−0.01 mg of CBC per individual dose.

Example 13

To prepare a bulk standard of ink, purified THC, purified β-Pinene, glycerin, ethanol, polyvinylpyrrolidone, and water are combined.

Purified THC was used at ≥50% purity as determined by HPLC.

Purified β-Pinene was used at ≥60% purity as determined by HPLC.

70 mL of purified THC and 3.0 mL of purified β-Pinene are combined with 7.0 mL of glycerin, 20 mL of ethanol, and 100 mg of polyvinylpyrrolidone to make an ink composition comprising of 70% THC by weight and 3% β-Pinene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 10 mg+/−1 mg of THC per individual dose.

Example 14

To prepare a bulk standard of ink, purified THC, purified β-Pinene, glycerin, ethanol, polyvinylpyrrolidone, and water are combined.

Purified THC is used at ≥60% purity as determined by HPLC.

Purified β-Pinene is used at ≥70% purity as determined by HPLC.

70 mL of purified THC and 3.0 mL of purified β-Pinene are combined with 7.0 mL of glycerin, 20 mL of ethanol, and 100 mg of polyvinylpyrrolidone to make an ink composition comprising of 70% THC by weight and 3% β-Pinene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 100 mg+/−5 mg of THC per individual dose.

Example 15

To prepare a bulk standard of ink, purified THC, purified β-Pinene, glycerin, ethanol, polyvinylpyrrolidone, and water are combined.

Purified THC was used at ≥70% purity as determined by HPLC.

Purified β-Pinene was used at ≥80% purity as determined by HPLC.

70 mL of purified THC and 3.0 mL of purified β-Pinene are combined with 7.0 mL of glycerin, 20 mL of ethanol, and 100 mg of polyvinylpyrrolidone to make an ink composition comprising of 70% THC by weight and 3% β-Pinene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 1 mg+/−0.01 mg of THC per individual dose.

Example 16

To prepare a bulk standard of ink, purified CBG, purified humulene, glycerin, ethanol, polyvinylpyrrolidone, and water are combined.

Purified CBG was used at ≥50% purity as determined by HPLC.

Purified humulene was used at ≥60% purity as determined by HPLC.

70 mL of purified CBG and 3.0 mL of purified humulene are combined with 7.0 mL of glycerin, 20 mL of ethanol, and 100 mg of polyvinylpyrrolidone to make an ink composition comprising of 70% CBG by weight and 3% humulene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 10 mg+/−1 mg of CBG per individual dose.

Example 17

To prepare a bulk standard of ink, purified CBG, purified humulene, glycerin, ethanol, polyvinylpyrrolidone, and water are combined.

Purified CBG is used at ≥60% purity as determined by HPLC.

Purified humulene is used at ≥70% purity as determined by HPLC.

70 mL of purified CBG and 3.0 mL of purified humulene are combined with 7.0 mL of glycerin, 20 mL of ethanol, and 100 mg of polyvinylpyrrolidone to make an ink composition comprising of 70% CBG by weight and 3% humulene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 100 mg+/−5 mg of CBG per individual dose.

Example 18

To prepare a bulk standard of ink, purified CBG, purified humulene, glycerin, ethanol, polyvinylpyrrolidone, and water are combined.

Purified CBG was used at ≥70% purity as determined by HPLC.

Purified humulene was used at ≥80% purity as determined by HPLC.

70 mL of purified CBG and 3.0 mL of purified humulene are combined with 7.0 mL of glycerin, 20 mL of ethanol, and 100 mg of polyvinylpyrrolidone to make an ink composition comprising of 70% CBG by weight and 3% humulene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 1 mg+/−0.01 mg of CBG per individual dose.

Example 19

To prepare a bulk standard of ink, purified CBD, purified linalool, glycerin, ethanol, polyvinylpyrrolidone, and water are combined.

Purified CBD was used at ≥50% purity as determined by HPLC.

Purified linalool was used at ≥60% purity as determined by HPLC.

70 mL of purified CBD and 3.0 mL of purified linalool are combined with 7.0 mL of glycerin, 20 mL of ethanol, and 100 mg of polyvinylpyrrolidone to provide an ink composition comprising of 70% CBD by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 10 mg+/−1 mg of CBD per individual dose.

Example 20

To prepare a bulk standard of ink, purified CBD, purified linalool, glycerin, ethanol, polyvinylpyrrolidone, and water are combined.

Purified CBD is used at ≥60% purity as determined by HPLC.

Purified linalool is used at ≥70% purity as determined by HPLC.

70 mL of purified CBD and 3.0 mL of purified linalool are combined with 7.0 mL of glycerin, 20 mL of ethanol, and 100 mg of polyvinylpyrrolidone to make an ink composition comprising of 70% CBD by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 100 mg+/−5 mg of CBD per individual dose.

Example 21

To prepare a bulk standard of ink, purified CBD, purified linalool, glycerin, ethanol, polyvinylpyrrolidone, and water are combined.

Purified CBD was used at ≥70% purity as determined by HPLC.

Purified linalool was used at ≥80% purity as determined by HPLC.

70 mL of purified CBD and 3.0 mL of purified linalool are combined with 7.0 mL of glycerin, 20 mL of ethanol, and 100 mg of polyvinylpyrrolidone to make an ink composition comprising of 70% CBD by weight and 3% linalool by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 1 mg+/−0.01 mg of CBD per individual dose.

Example 22

To prepare a bulk standard of ink, purified CBD, purified β-Pinene, glycerin, ethanol, polyvinylpyrrolidone, and water are combined.

Purified CBD was used at ≥50% purity as determined by HPLC.

Purified β-Pinene was used at ≥60% purity as determined by HPLC.

70 mL of purified CBD and 3.0 mL of purified β-Pinene are combined with 7.0 mL of glycerin, 20 mL of ethanol, and 100 mg of polyvinylpyrrolidone to make an ink composition comprising of 70% CBD by weight and 3% β-Pinene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 25 mg+/−2.5 mg of CBD per individual dose.

Example 23

To prepare a bulk standard of ink, purified CBD, purified β-Pinene, glycerin, ethanol, polyvinylpyrrolidone, and water are combined.

Purified CBD was used at ≥65% purity as determined by HPLC.

Purified β-Pinene was used at ≥75% purity as determined by HPLC.

70 mL of purified CBD and 3.0 mL of purified β-Pinene are combined with 7.0 mL of glycerin, 20 mL of ethanol, and 100 mg of polyvinylpyrrolidone to make an ink composition comprising of 70% CBD by weight and 3% β-Pinene by weight.

The ink composition was well mixed such that all the compounds were homogeneously dispersed within the ink composition. Water was only added in small increments (less than 5 mL at a time) to obtain a viscosity of 10 mPa·s.

The ink was loaded into an ink cartridge for a commercially available ink-jet printer. The composition was then printed onto water-soluble paper in a single layer in a continuous pattern such that the entire printable area is covered. The substrate was then moved to another printer with the ink of Example 1. A layer of THC/linalool is made by the same method of Example 1. The substrate was then divided into individual 35 mg (10 mg of THC and 25 mg of CBD) doses.

Example 24

To prepare a bulk standard of ink, purified CBC, purified caryophyllene oxide, glycerin, ethanol, polyvinylpyrrolidone, and water are combined.

Purified CBC was used at ≥65% purity as determined by HPLC.

Purified caryophyllene oxide was used at ≥75% purity as determined by HPLC.

70 mL of purified CBC and 3.0 mL of purified caryophyllene oxide are combined with 7.0 mL of glycerin, 20 mL of ethanol, and 100 mg of polyvinylpyrrolidone to make an ink composition comprising of 70% CBC by weight and 3% caryophyllene oxide by weight.

The ink composition was well mixed such that all the compounds were homogeneously dispersed within the ink composition. Water should only be added in small increments (less than 5 mL at a time) to obtain a viscosity of 10 mPa·s.

The ink was loaded into an ink cartridge for a commercially available ink-jet printer. The composition was then printed onto a sintered glass of 1 mm thickness and 5 mm×5 mm in a single layer in a continuous pattern such that the entire area is covered. The ink was then moved to a printer with the ink of Example 2. Then a layer of THC/linalool was made using the same method of Example 2. The glass was then used in a vaporizer and heated to create an inhalable vapor.

Example 25

To prepare a bulk standard of ink, purified CBC, purified α-Pinene, glycerin, ethanol, polyvinylpyrrolidone, and water are combined.

Purified CBC was used at ≥50% purity as determined by HPLC.

Purified α-Pinene was used at ≥60% purity as determined by HPLC.

70 mL of purified CBC and 3.0 mL of purified α-Pinene are combined with 7.0 mL of glycerin, 20 mL of ethanol, and 100 mg of polyvinylpyrrolidone to make an ink composition comprising of 70% CBC by weight and 3% α-Pinene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 25 mg+/−2.5 mg of CBC per individual dose.

Example 26

To prepare a bulk standard of ink, purified CBG, purified α-Pinene, glycerin, ethanol, polyvinylpyrrolidone, and water are combined.

Purified CBG was used at ≥65% purity as determined by HPLC.

Purified α-Pinene was used at ≥75% purity as determined by HPLC.

70 mL of purified CBG and 3.0 mL of purified α-Pinene are combined with 7.0 mL of glycerin, 20 mL of ethanol, and 100 mg of polyvinylpyrrolidone to make an ink composition comprising of 70% CBG by weight and 3% α-Pinene by weight.

The ink composition was well mixed such that all the compounds were homogeneously dispersed within the ink composition. Water was added in small increments (less than 5 mL at a time) to obtain a viscosity of 10 mPa·s.

The ink was loaded into an ink cartridge for a commercially available ink-jet printer. The composition was then printed onto water-soluble paper in a single layer in a continuous pattern such that the entire printable area is covered. The substrate was then moved to another printer with the ink of Example 1. A layer of THC/linalool was made by the same method of Example 1. The substrate was then divided into individual 35 mg (10 mg of THC and 25 mg of CBG) doses.

Example 27

To prepare a bulk standard of ink, purified CBG, purified caryophyllene oxide, glycerin, ethanol, polyvinylpyrrolidone, and water are combined.

Purified CBG was used at ≥65% purity as determined by HPLC.

Purified caryophyllene oxide was used at ≥75% purity as determined by HPLC.

70 mL of purified CBG and 3.0 mL of purified caryophyllene oxide are combined with 7.0 mL of glycerin, 20 mL of ethanol, and 100 mg of polyvinylpyrrolidone to make an ink composition comprising of 70% CBG by weight and 3% caryophyllene oxide by weight.

The ink composition was well mixed such that all the compounds were homogeneously dispersed within the ink composition. Water was only added in small increments (less than 5 mL at a time) to obtain a viscosity of 10 mPa·s.

The ink was loaded into an ink cartridge for a commercially available ink jet printer. The composition was then printed onto a sintered glass of 1 mm thickness and 5 mm×5 mm in a single layer in a continuous pattern such that the entire area is covered. The ink was then moved to a printer with the ink of Example 2. Then a layer of THC/linalool was made using the same method of Example 2. The glass was used in a vaporizer and heated to create an inhalable vapor.

Example 28

To prepare a bulk standard of ink, purified CBD, purified α-Pinene, glycerin, ethanol, polyvinylpyrrolidone, and water are combined.

Purified CBD was used at ≥50% purity as determined by HPLC.

Purified α-Pinene was used at ≥60% purity as determined by HPLC.

70 mL of purified CBD and 3.0 mL of purified α-Pinene are combined with 7.0 mL of glycerin, 20 mL of ethanol, and 100 mg of polyvinylpyrrolidone to make an ink composition comprising of 70% CBD by weight and 3% α-Pinene by weight.

The ink composition was well mixed such that all the compounds were homogeneously dispersed within the ink composition. Water was only added in small increments (less than 5 mL at a time) to obtain a viscosity of 10 mPa·s.

The prepared ink composition was weighed and loaded into an ink cartridge for a commercially available ink-jet printer. The composition was then printed onto water-soluble paper in a single layer in a continuous pattern such that substantially all of the printable area was covered. The paper was then divided into individual doses having 25 mg+/−2.5 mg of CBD per individual dose.

Example 29

To prepare a bulk standard of ink, purified CBD, purified α-Pinene, glycerin, ethanol, polyvinylpyrrolidone, and water are combined.

Purified CBD was used at ≥65% purity as determined by HPLC.

Purified α-Pinene was used at ≥75% purity as determined by HPLC.

70 mL of purified CBD and 3.0 mL of purified α-Pinene are combined with 7.0 mL of glycerin, 20 mL of ethanol, and 100 mg of polyvinylpyrrolidone to make an ink composition comprising of 70% CBD by weight and 3% α-Pinene by weight.

The ink composition was well mixed such that all the compounds were homogeneously dispersed within the ink composition. Water was only added in small increments (less than 5 mL at a time) to obtain a viscosity of 10 mPa·s.

The ink was loaded into an ink cartridge for a commercially available ink-jet printer. The composition was then printed onto water-soluble paper in a single layer in a continuous pattern such that the entire printable area is covered. The substrate was then moved to another printer with the ink of Example 1. A layer of THC/linalool was made by the same method of Example 1. The substrate was then divided into individual 35 mg (10 mg of THC and 25 mg of CBD) doses.

Example 30

To prepare a bulk standard of ink, purified CBC, purified caryophyllene oxide, glycerin, ethanol, polyvinylpyrrolidone, and water are combined.

Purified CBC was used at ≥65% purity as determined by HPLC.

Purified caryophyllene oxide was used at ≥75% purity as determined by HPLC.

70 mL of purified CBC and 3.0 mL of purified caryophyllene oxide are combined with 7.0 mL of glycerin, 20 mL of ethanol, and 100 mg of polyvinylpyrrolidone to make an ink composition comprising of 70% CBC by weight and 3% caryophyllene oxide by weight.

The ink composition was well mixed such that all the compounds were homogeneously dispersed within the ink composition. Water was only added in small increments (less than 5 mL at a time) to obtain a viscosity of 10 mPa·s.

The ink was loaded into an ink cartridge for a commercially available ink jet printer. The composition was printed onto a sintered glass of 1 mm thickness and 5 mm×5 mm in a single layer in a continuous pattern such that the entire area is covered. The ink was then moved to a printer with the ink of Example 4. Then a layer of THC/humulene was made using the same method of Example 4. The glass was then placed in a vaporizer and heated to create an inhalable vapor.

We claim:

1. A printable ink composition, comprising:
   a purified cannabinoid, wherein the purified cannabinoid is chosen from THC, CBD, CBC, CBG, or THCV;
   a purified terpene, wherein the purified terpene is chosen from α-bisabolol, β-bisabolol, borneol, carene (Δ-3-carene), camphene, caryophyllene (β-caryophyllene), caryophyllene oxide, P-cymene, eucalyptol, eugenol, farnesol, geraniol, humulene (α-humulene) (β-humulene), limonene, linalool, myrcene (β-myrcene), nerolidol, ocimene, phellandrene, phytol, α-pinene, β-pinene, pulegone, sabinene, α-terpinene, γ-terpinene, terpineol or terpinolene;
   an excipient; and
   a solvent, wherein the solvent is one or more of water, glycerin, ethanol and polyvinylpyrrolidone,
   wherein the ink composition is a liquid at room temperature.

2. The printable ink composition of claim 1, which has a viscosity of about 10 mPa·s.

3. The printable ink composition of claim 1, wherein, when printed on a substrate by an inkjet printer, the printable ink composition is capable of providing consistently dosed substrates of the purified cannabinoid.

4. The printable ink composition of claim 3, wherein the printable ink composition is capable of providing consistently dosed substrates when printed in a single layer.

5. The printable ink composition of claim 3, wherein the substrate is a water soluble substrate.

6. The printable ink composition of claim 3, wherein the substrate is an inert substrate.

7. The printable ink composition of claim 6, wherein the inert substrate is stable at elevated temperatures.

8. The printable ink composition of claim 1, wherein the purified cannabinoid is THC and the purified terpene is linalool.

9. A comprising:
   a) a printed ink, wherein the printed ink is from a printable ink composition comprising:
      a purified cannabinoid, wherein the purified cannabinoid is chosen from THC, CBD, CBC, CBG, or THCV;
      a purified terpene, wherein the purified terpene is chosen from α-bisabolol, β-bisabolol, borneol, carene (Δ-3-carene), camphene, caryophyllene (β-caryophyllene), caryophyllene oxide, P-cymene, eucalyptol, eugenol, farnesol, geraniol, humulene (α-humulene) (β-humulene), limonene, linalool, myrcene (β-myrcene), nerolidol, ocimene, phellandrene, phytol, α-pinene, β-pinene, pulegone, sabinene, α-terpinene, γ-terpinene, terpineol or terpinolene;
      an excipient; and
      a solvent, wherein the solvent is one or more of water, glycerin, ethanol and polyvinylpyrrolidone,
      wherein the printable ink composition is a liquid at room temperature; and
   b) a substrate.

10. The product of claim 9, wherein the is a water soluble substrate.

11. The product of claim 9, wherein the is an inert substrate.

12. The product of claim 11, wherein the inert substrate is stable at elevated temperatures.

* * * * *

UNITED STATES PATENT AND TRADEMARK OFFICE
CERTIFICATE OF CORRECTION

PATENT NO. : 10,821,147 B2
APPLICATION NO. : 16/060007
DATED : November 3, 2020
INVENTOR(S) : Jonathan Michael Cooper and Kurt Aron Levy It is certified that error appears in the above-identified patent and that said Letters Patent is hereby corrected as shown below:

On the Title Page

Item (60), please delete:
"Provisional application No. 62/354,463, filed on Jun. 24, 2016, provisional application No. 62/348,114, filed on Jun. 9, 2016, provisional application No. 62/347,558, filed on Jun. 8, 2016, provisional application No. 62/264,281, filed on Dec. 7, 2015."
And insert:
--Provisional application No. 62/369,932, filed on Aug. 2, 2016, provisional application No. 62/354,463, filed on Jun. 24, 2016, provisional application No. 62/348,114, filed on Jun. 9, 2016, provisional application No. 62/347,558, filed on Jun. 8, 2016, provisional application No. 62/264,281, filed on Dec. 7, 2015.--

In the Specification

Column 1, Lines 7-17, please delete:
"This application is being filed under 35 U.S.C. 371 and is the National Stage of International Application No. PCT/US2016/065455 filed Dec. 7, 2016, which claims priority under 35 U.S.C. 119 to U.S. Provisional Application No. 62/349,932, filed Aug. 2, 2016; 62/354,463 filed Jun. 24, 2016; 62/348,114 filed Jun. 9, 2016; and 62/347,558 filed Jun. 8, 2016; and is a continuation of U.S. application Ser. No. 15/055,499, filed Feb. 26, 2016, which claims priority to U.S. Provisional Application No. 62/264,281 filed Dec. 7, 2015, which are herein incorporated by reference in their entireties."
And insert:
--This application is a National Stage application under 35 U.S.C. 371 of International Application No. PCT/US2016/065455 having an international filing date of Dec. 7, 2016, which designated the United States and which claims priority under 35 U.S.C. 119 to U.S. Provisional Application Nos.: 62/369,932, filed Aug. 2, 2016; 62/354,463 filed Jun. 24, 2016; 62/348,114 filed Jun. 9, 2016; 62/347,558 filed Jun. 8, 2016; and 62/264,281 filed Dec. 7, 2015; and is a continuation of U.S. application Ser. No. 15/055,499, filed Feb. 26, 2016, all of which are herein incorporated by reference in their entireties.--

Signed and Sealed this
Sixth Day of April, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,821,147 B2

In the Claims

Column 32, Claim 10, Lines 37-38, please delete:
"The product of claim 9, wherein the is a water soluble substrate."
And insert:
--The product of claim 9, wherein the substrate is a water soluble substrate.--

Column 32, Claim 11, Lines 39-40, please delete:
"The product of claim 9, wherein the is an inert substrate"
And insert:
--The product of claim 9, wherein the substrate is an inert substrate.--